United States Patent [19]

Jerusalmy

[11] Patent Number: 5,711,315
[45] Date of Patent: Jan. 27, 1998

[54] SINUS LIFT METHOD

[76] Inventor: Israel Jerusalmy, 6 Kissufim Street, Tel Aviv 69355, Israel

[21] Appl. No.: 601,708

[22] Filed: Feb. 15, 1996

[51] Int. Cl.$^6$ .................................................. A61B 19/00
[52] U.S. Cl. ........................... 128/898; 433/173; 433/167
[58] Field of Search ..................................... 433/173, 167, 433/172, 174, 180, 215; 128/898

[56] References Cited

PUBLICATIONS

Smiler, D.G., et al., Sinus Lift Grafts and Endosseous Implants: Treatment of the Atrophic Posterior Maxilla, *Dental Clinics of North America*, 1992, vol. 36, No. 1, pp.151–163, 178–186.
Adell, R., et al., A 15–year study of osseointegrated implants in the treatment of the edentulous jaw, *Int. J. Oral Surg.*, 1981, vol. 10, pp. 387–416.
Rosenlicht, J.L., Sinus lift procedure (subantral augmentation), *Implants: Clinical Reviews in Dentistry*, 1992, vol. 1, No. 1, pp. 1–8.
Bonefit® Original ITI–Dental Implants: Clinical Procedure, *Institut Straumann Dental* (brochure).
Membrane Symposium 1993: 5 Years of Guided Bone Regeneration in Implant Dentistry, (program).
Rudert, H., *Microscopic and endoscopic endonasal surgery of the paranasal sinuses*, University of Kiel, Federal Republic of Germany.
Stammberger, H., *Functional endoscopic nasal and paranasal sinus surgery: The Messerklinger Technique (MT)*, University Ear, Nose and Throat Hospital, Austria.
Godefroy, J.N., et al., Ridge reconstruction after implant failure using a resorbable membrane: Report of a case and histologic study, *The International Journal of Oral & Maxillofacial Implants*, 1994, vol. 9, No. 4, pp. 431–435.
Paroguide® The resorbible membrane for regeneration of tissue, *Coletica* (brochure).
Brunel, et al., Resorbable membrane and periodontal regeneration: Experimental study on the Beagle dog, *Lebanese Dental Journal*, 1994, vol. 33, No. 2, pp 172–181.
Storz The World of Endoscopy: Endoscopes and Instruments for Otology, 1994, 5th edition.

*Primary Examiner*—Vincent Millin
*Assistant Examiner*—Kelly R. O'Hara
*Attorney, Agent, or Firm*—Helfgott & Karas, PC.

[57] ABSTRACT

A method for subantral augmentation including the steps of lifting the schneiderian membrane from the antral floor, and placing graft material between the schneiderian membrane and the antral floor, without fracturing the lateral maxillary wall.

1 Claim, 5 Drawing Sheets

SINUS LIFT METHOD

FIELD OF THE INVENTION

The present invention relates to methods for dental implantology generally, and particularly for subantral augmentation.

BACKGROUND OF THE INVENTION

Treatment of edentulous patients with osseointegrated fixtures made of titanium is a well known procedure in the art. The procedure includes installing a fixture in the alveolar bone of an at least partially edentulous jaw. Usually about 4 months are required for proper healing after fixture installation in the mandible, while about six months are required after installation in the maxilla.

After healing, an abutment is installed on the upper portion of the fixture. After about two weeks, an artificial tooth may be screwed on to the abutment and the procedure is completed.

A review of osseointegrated implantology may be found in "A Fifteen Year Study of Osseointegrated Implants in the Treatment of the Edentulous Jaw", R. Adell et al., Int. J. Oral Surg., 1981, 10:387–416.

Installation of implants requires sufficient alveolar bone height, generally about 10 mm, for the implant fixture to be properly osseointegrated. Various factors may cause a lack of available alveolar bone height, e.g., a thin edentulous maxillary alveolar ridge, especially in the area of the free end, a flat palate or atrophic maxillary alveolus. In order to create increased bone height, the subantral augmentation technique, popularly known as the sinus lift technique, was developed, the first such procedure being introduced by Dr. Hilt Tatum of the United States in 1975.

A summary of the prior art method of subantral augmentation is described hereinbelow. The prior art requires cutting a "trapdoor" in the lateral maxillary wall and causing greenstick fracture thereof.

SUMMARY OF THE INVENTION

The present invention seeks to provide improved methods for subantral augmentation. Unlike the prior art, which is an open procedure, the present invention is a closed procedure. The present invention does not cut a "trapdoor" in the lateral maxillary wall and does not require a greenstick fracture thereof.

There is thus provided in accordance with a preferred embodiment of the present invention, a method for subantral augmentation without osteotomy including the steps of lifting the schneiderian membrane from the antral floor, and placing graft material between the schneiderian membrane and the antral floor.

In accordance with a preferred embodiment of the present invention, the method includes the step of drilling a hole in the lateral maxillary wall, wherein the schneiderian membrane is lifted by a tool introduced through the hole. The graft material may be introduced through this hole.

Additionally in accordance with a preferred embodiment of the present invention, the method further includes the step of providing optical apparatus in the maxillary sinus region.

Further in accordance with a preferred embodiment of the present invention, the method includes the step of placing a resorbable membrane on at least one of the antral floor and the schneiderian membrane before the step of placing graft material between the schneiderian membrane and the antral floor.

The graft material is intended to create a temporary stable structure which supports the resorbable membrane on top of which rests the schneiderian membrane.

Alternatively, in accordance with a preferred embodiment of the present invention, the schneiderian membrane is lifted by grasping the membrane with a tool introduced through the maxillary sinus, and wherein the graft material is introduced via the maxillary sinus through an incision in the schneiderian membrane, the incision being subsequently packed by a portion of the graft material.

BRIEF DESCRIPTION OF THE DRAWINGS

The present invention will be understood and appreciated from the following detailed description, taken in conjunction with the drawings in which.

DETAILED DESCRIPTION OF PREFERRED EMBODIMENTS

Figure 1:
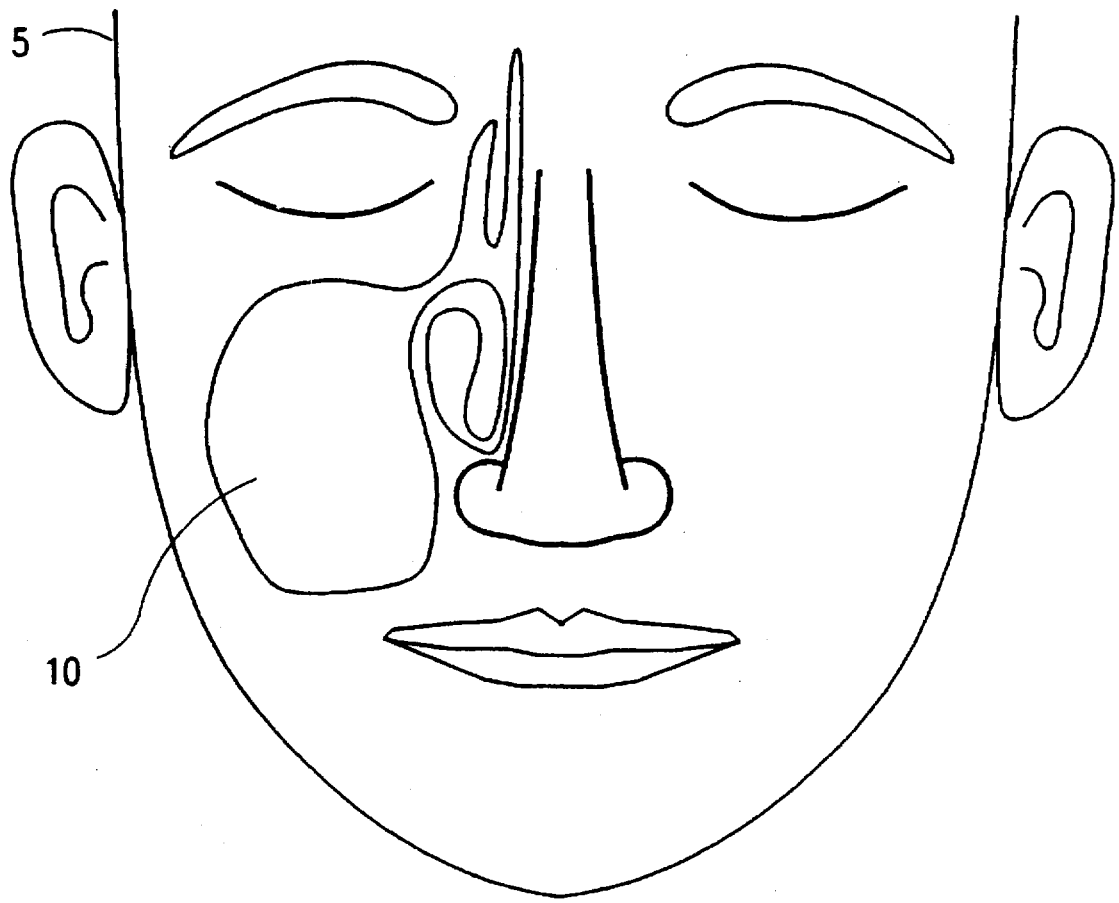
FIG. 1 is a simplified, front view illustration of a human face, showing the position of the maxillary sinus.
Figure 2:
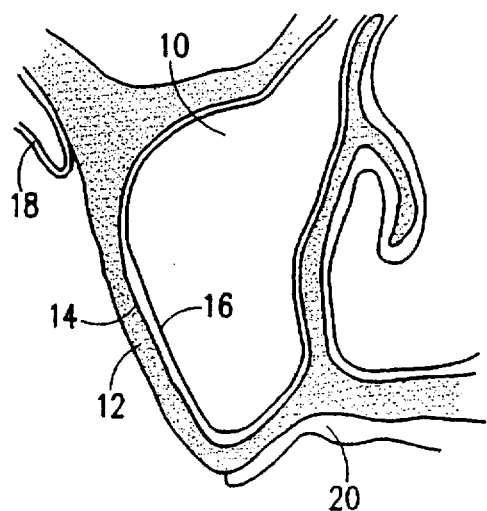
FIG. 2 is a simplified, sectional illustration of the maxillary sinus, lateral maxillary wall, antral floor, schneiderian membrane and reflected mucoperiosteal flap.

Anatomy of the maxillary sinus region will now be briefly described with reference to FIGS. 1 and 2. FIG. 1 is a simplified, front view illustration of a human face 5, showing the position of the maxillary sinus 10. FIG. 2 is a simplified, sectional illustration of the maxillary sinus 10, clearly showing the lateral maxillary wall 12, the antral floor 14, schneiderian membrane 16 and reflected mucoperiosteal flap 18. The remaining portion of the mucoperiosteal flap is shown at reference numeral 20. The antral floor 14 is simply the medial side of the maxillary wall. The schneiderian membrane 16 covers the inner surface of the maxillary sinus 10, and is also known as the sinus membrane.

Figure 3:
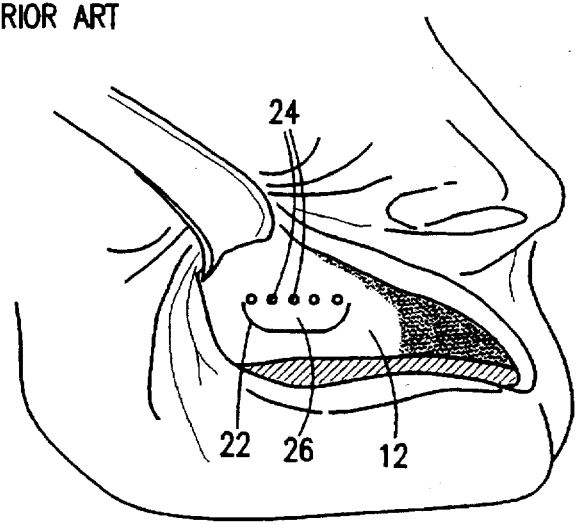
FIG. 3 is a simplified pictorial illustration of an arcuate osteotomy performed during a prior art subantral augmentation.

The prior art method of subantral augmentation is now described with reference to FIGS. 3–5. As seen in FIG. 3, an osteotomy 22 of the lateral maxillary wall 12 is made, taking care not to damage the schneiderian membrane (not seen in FIG. 3). The osteotomy 22 may be arcuate as shown in FIG. 3, or may be rectangular. A plurality of holes 24 are drilled in the lateral maxillary wall 12, superior to the osteotomy 22. The osteotomy 22 and holes 24 together form the outline of a "trapdoor" 26.

Figure 4:
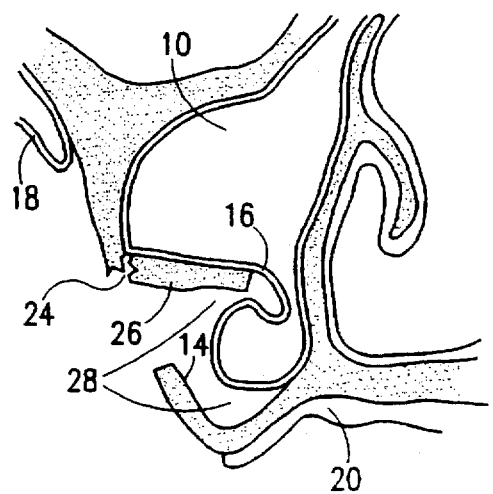
FIG. 4 is a simplified sectional illustration of fracturing the antral floor medially during the prior art subantral augmentation.

In FIG. 4, trapdoor 26 is greenstick-fractured medially along the location of holes 24. The schneiderian membrane 16 is lifted away from the antral floor 14, creating a subantral space 28.

Figure 5:
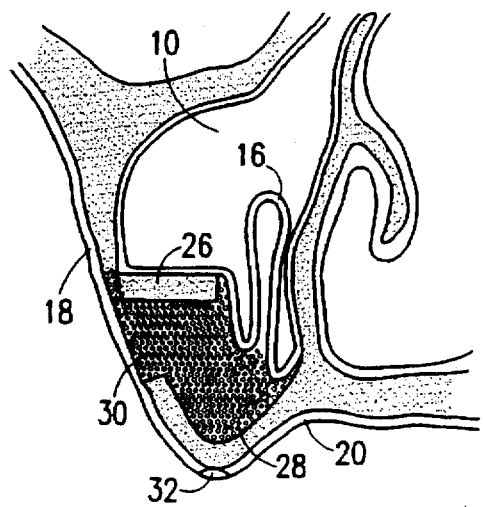
FIG. 5 is a simplified sectional illustration of the subantral space filled with graft material and the mucoperiosteal flap sutured, according to the prior art subantral augmentation.

In FIG. 5, the subantral space 28 is filled with graft material 30 and the two portions 18 and 20 of the mucoperiosteal flap are sutured at reference numeral 32. After osseointegration of the graft material 30 and sufficient healing, the subantral space 28 is sufficiently augmented for placement of implants (not shown). Sometimes the implants may be placed concomitantly with the graft material 30.

Reference is now made to FIGS. 6–9 which illustrate subantral augmentation performed in accordance with a preferred embodiment of the present invention.

Figure 6:
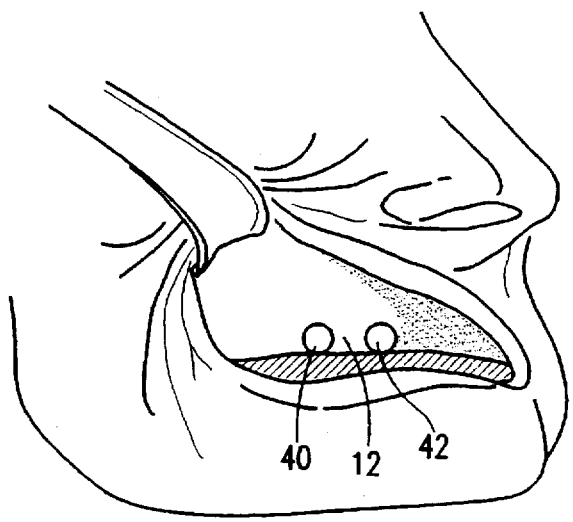
FIG. 6 is a simplified pictorial illustration of two holes drilled in the lateral maxillary wall during subantral augmentation performed in accordance with a preferred embodiment of the present invention.

In accordance with a preferred embodiment of the present invention, as shown in FIG. 6, two holes 40 and 42 may be drilled in the lateral maxillary wall 12. Preferably, care is exercised not to perforate the schneiderian membrane (not shown in FIG. 6). However, it is not essential to maintain the schneiderian membrane free of perforations, as will be appreciated hereinbelow with reference to FIGS. 7 and 8. Moreover, in accordance with another preferred embodiment of the present invention, the maxillary wall does not have to be damaged at all, as will be described hereinbelow with reference to FIGS. 10 and 11.

Figure 7:
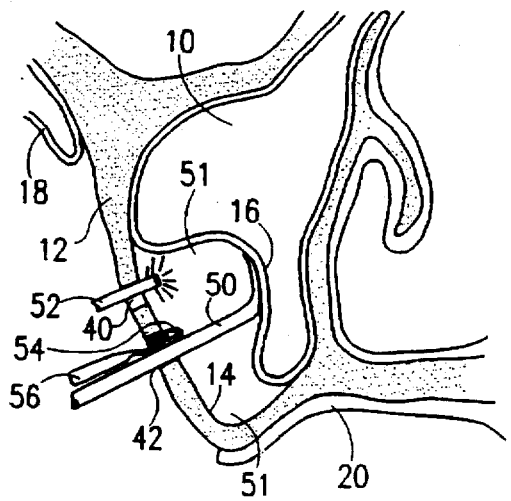
FIG. 7 is a simplified sectional illustration of lifting the schneiderian membrane and inserting a resorbable membrane, in accordance with a preferred embodiment of the present invention.

Reference is now made to FIG. 7. A tool, such as a freer elevator 50 may be inserted through hole 42 and used to lift the schneiderian membrane 16 from the antral floor 14, thereby creating a subantral space 51. Alternatively, the schneiderian membrane 16 may be separated from and lifted away from the antral floor 14 by other suitable means.

Illumination and/or optical observation apparatus, such as endoscopic apparatus 52, may be inserted through hole 40, as shown in FIG. 7. A resorbable membrane 54 may be inserted through hole 42 by means of an insertion tool 56. Resorbable membrane 54 may be made, for example, of collagen or of Paroguide brand membrane, manufactured by Coletica of France. Resorbable membrane 54 is shown in FIG. 7 in rolled or bunched form for easy insertion through hole 42. After insertion, the membrane 54 is preferably spread below the schneiderian membrane 16. Another resorbable membrane (not shown) may also be spread along the antral floor 14, if needed.

Small holes (not shown) may be drilled in the area of the inferior maxillary wall 12 to aid in osseointegration of graft material 60.

Figure 8:
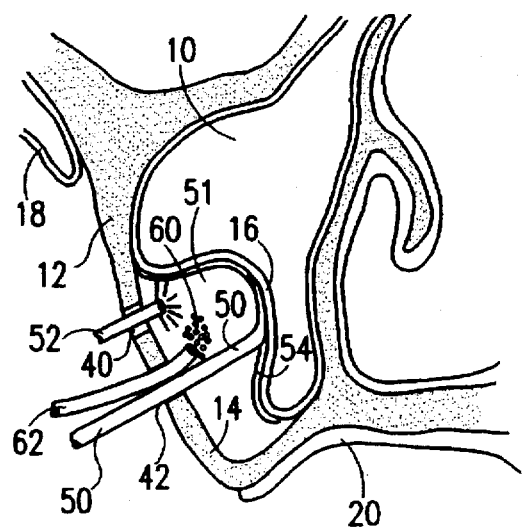
FIG. 8 is a simplified sectional illustration of filling the subantral space with graft material, in accordance with a preferred embodiment of the present invention.

In FIG. 8, the subantral space 51 is filled with graft material 60, preferably introduced, such as by injection through a hollow cannula 62 inserted through hole 42. Alternatively, graft material 60 may be introduced directly through hole 42. Graft material 60 may be, for example, small rolls or particles of collagen or fibrin, perhaps coated with hydroxyapatite, and autogenous particles, such as from the maxillary tuberosity, mixed with blood. The graft material 60 supports the schneiderian membrane 16 during and after filling of the subantral space 51. Any tears or perforations in the schneiderian membrane 16 may be packed by graft material 60.

Figure 9:
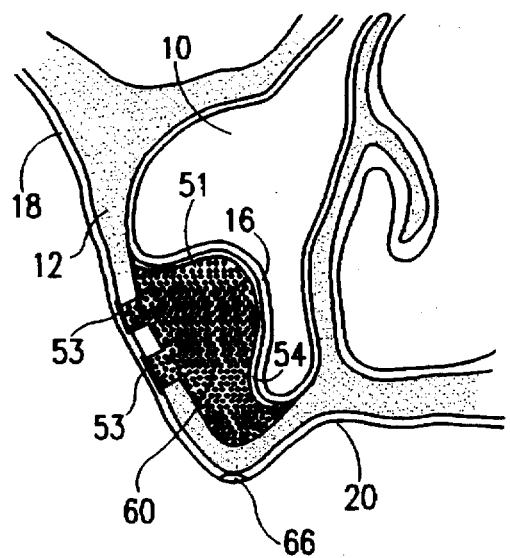
FIG. 9 is a simplified sectional illustration of the subantral space filled with graft material and the mucoperiosteal flap sutured, in accordance with a preferred embodiment of the present invention.

In FIG. 9, the subantral space 51 has been completely filled with graft material 60. Preferably an additional resorbable membrane 53 may be placed against the lateral surface of the lateral maxillary wall 12, thereby helping to seal holes 40 and 42. The two portions 18 and 20 of the mucoperiosteal flap may then be sutured at reference point 66.

Thus, the present invention provides a closed technique for subantral augmentation, in contrast with the prior art which requires opening a trapdoor in the lateral maxillary wall.

It is appreciated that instead of drilling two holes 40 and 42, one single enlarged hole 42 may be drilled which is sufficient for also passing therethrough endoscopic apparatus 52.

As mentioned hereinabove, in accordance with another preferred embodiment of the present invention, the maxillary wall 12 does not have to be damaged at all, as is now described with reference to FIGS. 10 and 11.

Figure 10:
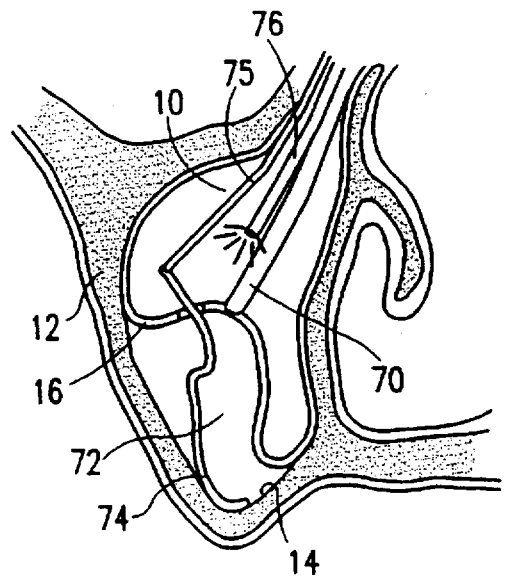
FIG. 10 is a simplified sectional illustration of lifting the schneiderian membrane and inserting a resorbable membrane, in accordance with another preferred embodiment of the present invention.

Instead of drilling holes in the lateral maxillary wall, a tool, such as a flexible, and preferably articulated, membrane elevator 70, may be inserted into the maxillary sinus 10, such as through one of the nostrils (not shown in FIG. 10), and be used to grip and lift the schneiderian membrane 16 from the antral floor 14, thereby creating a subantral space 72, as seen in FIG. 10. A resorbable membrane 74 may be introduced by another tool 75 into the maxillary sinus 10, such as through the same nostril, and spread along the antral floor 14. An incision may have to be made in the schneiderian membrane 16 to allow placement of the resorbable membrane 74. Endoscopic apparatus 76 may be inserted through the nostril (not shown).

Figure 11:
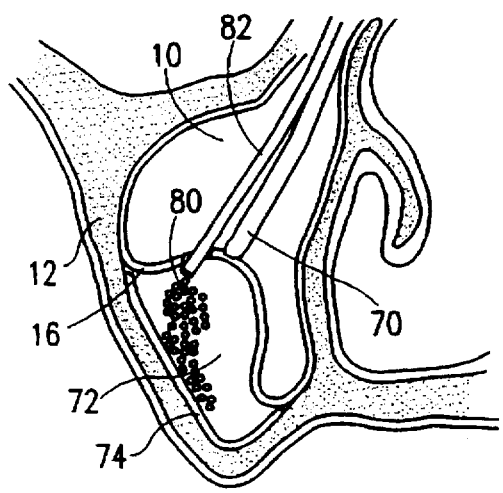
FIG. 11 is a simplified sectional illustration of filling the subantral space with graft material, in accordance with another preferred embodiment of the present invention.

Reference is now made to FIG. 11. In a similar fashion as described hereinabove with reference to FIG. 8, subantral space 72 may be filled with graft material 80, preferably introduced through a hollow tube 82 inserted through one of the nostrils (not shown). Any tears or perforations in the schneiderian membrane 16 may be packed by graft material 80. The subantral space 72 may be completely filled with graft material 80 which becomes osseointegrated with the maxillary wall 12.

It is appreciated that various features of the invention which are, for clarity, described in the contexts of separate embodiments may also be provided in combination in a single embodiment. Conversely, various features of the invention which are, for brevity, described in the context of a single embodiment may also be provided separately or in any suitable subcombination.

It will be appreciated by persons skilled in the art that the present invention is not limited to what has been particularly shown and described hereinabove. Rather, the scope of the present invention is defined only by the claims that follow:

I claim:

1. A method for subantral augmentation without osteotomy comprising the steps of:

lifting the schneiderian membrane from the antral floor; and placing graft material between the schneiderian membrane and the antral floor; and wherein the schneiderian membrane is lifted by grasping said membrane with a tool introduced through the maxillary sinus, and wherein said graft material is introduced via the maxillary sinus through an incision in the schneiderian membrane, said incision being subsequently packed by a portion of said graft material.

* * * * *